US009519269B2

(12) United States Patent
Han et al.

(10) Patent No.: US 9,519,269 B2
(45) Date of Patent: Dec. 13, 2016

(54) HIGH FREQUENCY PIEZOELECTRIC CRYSTAL COMPOSITES, DEVICES, AND METHODS FOR MANUFACTURING THE SAME

(75) Inventors: Pengdi Han, Bolingbrook, IL (US); Jian Tian, Bolingbrook, IL (US); Kevin Meneou, Bolingbrook, IL (US); Brandon Stone, Bolingbroke, IL (US)

(73) Assignee: CTS CORPORATION, Lisle, IL (US)

( * ) Notice: Subject to any disclaimer, the term of this patent is extended or adjusted under 35 U.S.C. 154(b) by 628 days.

(21) Appl. No.: 13/821,400

(22) PCT Filed: Oct. 13, 2011

(86) PCT No.: PCT/US2011/056230
§ 371 (c)(1),
(2), (4) Date: Apr. 23, 2013

(87) PCT Pub. No.: WO2012/051464
PCT Pub. Date: Apr. 19, 2012

(65) Prior Publication Data
US 2013/0211251 A1 Aug. 15, 2013

Related U.S. Application Data

(60) Provisional application No. 61/344,801, filed on Oct. 13, 2010.

(51) Int. Cl.
*H01L 41/187* (2006.01)
*G03H 3/00* (2006.01)
(Continued)

(52) U.S. Cl.
CPC ........ *G03H 3/00* (2013.01); *A61B 8/00* (2013.01); *C01G 33/006* (2013.01); *C30B 29/30* (2013.01); *C30B 29/32* (2013.01); *H01L 41/18* (2013.01); *H01L 41/183* (2013.01); *H01L 41/332* (2013.01); *H01L 41/338* (2013.01); *C01P 2002/50* (2013.01); *C01P 2004/03* (2013.01)

(58) Field of Classification Search
CPC ........................................................ H01B 3/12
USPC ...... 310/358; 252/62.9 PZ, 62.9 R; 501/134; 264/435, 436
See application file for complete search history.

(56) References Cited

U.S. PATENT DOCUMENTS 7,622,853 B2   11/2009  Rehrig et al.
2002/0130591 A1   9/2002  Fraser
(Continued)

OTHER PUBLICATIONS

Korean Appln. Serial No. 10-2013-7007909, Notice of Preliminary Rejection mailed Nov. 19, 2015, 2 pgs.—English, 4 pgs.—Korean.
(Continued)

*Primary Examiner* — Thomas Dougherty
(74) *Attorney, Agent, or Firm* — Daniel Deneufbourg

(57) ABSTRACT

The present invention generally relates to high frequency piezoelectric crystal composites, devices, and method for manufacturing the same. In adaptive embodiments an improved imaging device, particularly a medical imaging device or a distance imaging device, for high frequency (>20 MHz) applications involving an imaging transducer assembly is coupled to a signal imagery processor. Additionally, the proposed invention presents a system for photolithography based micro-machined piezoelectric crystal composites and their uses resulting in improved performance parameters.

6 Claims, 9 Drawing Sheets

(51) Int. Cl.

| | |
|---|---|
| A61B 8/00 | (2006.01) |
| C01G 33/00 | (2006.01) |
| H01L 41/18 | (2006.01) |
| H01L 41/332 | (2013.01) |
| H01L 41/338 | (2013.01) |
| C30B 29/30 | (2006.01) |
| C30B 29/32 | (2006.01) |

(56) References Cited

U.S. PATENT DOCUMENTS

| | | | |
|---|---|---|---|
| 2008/0012054 A1* | 1/2008 | Ifuku | B41J 2/14233 257/295 |
| 2009/0194732 A1 | 8/2009 | Luo et al. | |
| 2010/0152587 A1 | 6/2010 | Haider et al. | |
| 2010/0168582 A1 | 7/2010 | Yuan et al. | |

OTHER PUBLICATIONS

High Temperature Morphotropic Phase Boundary Piezoelectrics, Edward F., et al., 2003 IEEE ULtrasonics, 2003, 4 pgs.—English.
PIN-PMN-PT Single Crystal High Frequency Ultrasound Transducers for Medical Applications, Q. F. Zhou, et al., 2008, IEEE International Ultrasonics Symposium Proceedings, pp. 1433-1436, English.
Haixia Wang et al., Elecric property of single-crystal PMN-31% Pt/epoxy 1-3 piezoelectric composites. Physica Status solidi(a). Nov. 4, 2005, vol. 202, No. 14, pp. 2829-2835.
Q.F. Zhou, et al. "PIN-PMN-PT Single Crystal High Frequency Ultrasound Transducers for Medical Appliations." In: 2008 IEEE International Ultrasoncis Symposium. Nov. 2008, pp. 1433-1436.
Ping Sun. Design and Fabrication of PIN-PMN-Pt Single Crystal High-Frequency Ultrasound Transducers. IEEE. Transactions on Ultrasonics, Ferroelectrics, and Frequency Control., Dec. 2009, vol. 56, No. 12, pp. 2760-2763.
Tian, et al. "Piezoelectric Crystal Composite for High Frequency Ultrasound Application" In: 2010 IEEE International Ultrasonics Symposium Oct. 11-14, 2010, pp. 1-15.
Tian, et al. "Piezoelectric Crystal Composite for High Frequency Ultrasound Application" In: 2010 IEEE International Ultrasonics Symposium Proceedings, Nov. 9, 2010, pp. 65-67.
Wang,et al. "Deep Reactive Ion Etching of Lead Zirconate Titanate Using Sulfur Hexafluoride Gas", In: J. Am. Ceram. Soc., May 1999, pp. 1339-1341.
Efremov, et al. "Etching Mechanism of Pb(Zr,Ti)O$_3$ Thin Films in Cl$_2$/Ar Plasma" In: Plasma Chemistry and Plasma Processing. vol. 24 No. Mar. 1, 2004, pp. 13-28.
PCT/US2011/056230 ISR and Written Opinion mailed May 29, 2012, 13 pages.
PCT/US2011/056231 ISR and Written Opinion mailed May 29, 2012, 7 pages.
High Temperature Morphotropic Phase Boundary Piezoelectrics, Alberta, Rehrig, Flackenberger, TRS Technologies, Inc., Randall and Shrout, Materials Research Institute, 2003 IEEE Ultrasoncis Symposium-1991, 1992, 1993, 1994, 4 pages.
PCT/US2011/056230, Notification Concerning Transmittal of IPR on Patentability mailed Apr. 25, 2013, 6 pages.

* cited by examiner $$d'_{31} = d_{31} * \text{Cos}(\theta) * \text{Cos}(\theta) + d_{32} * \text{Sin}(\theta) * \text{Sin}(\theta)$$

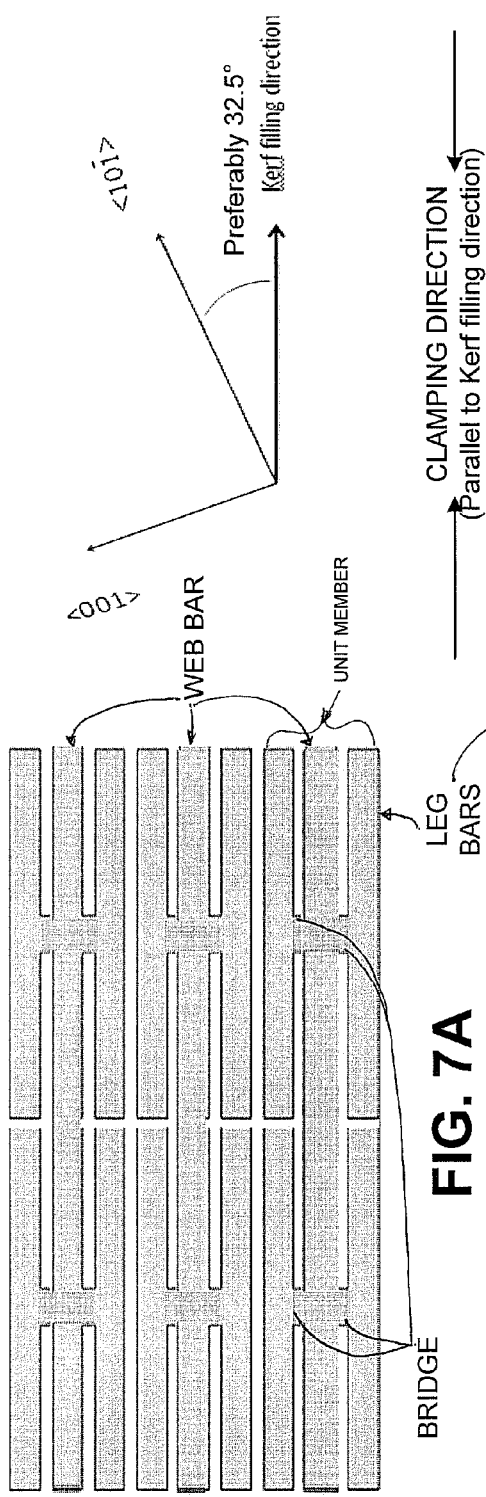
FIG. 7A
FIG. 7B
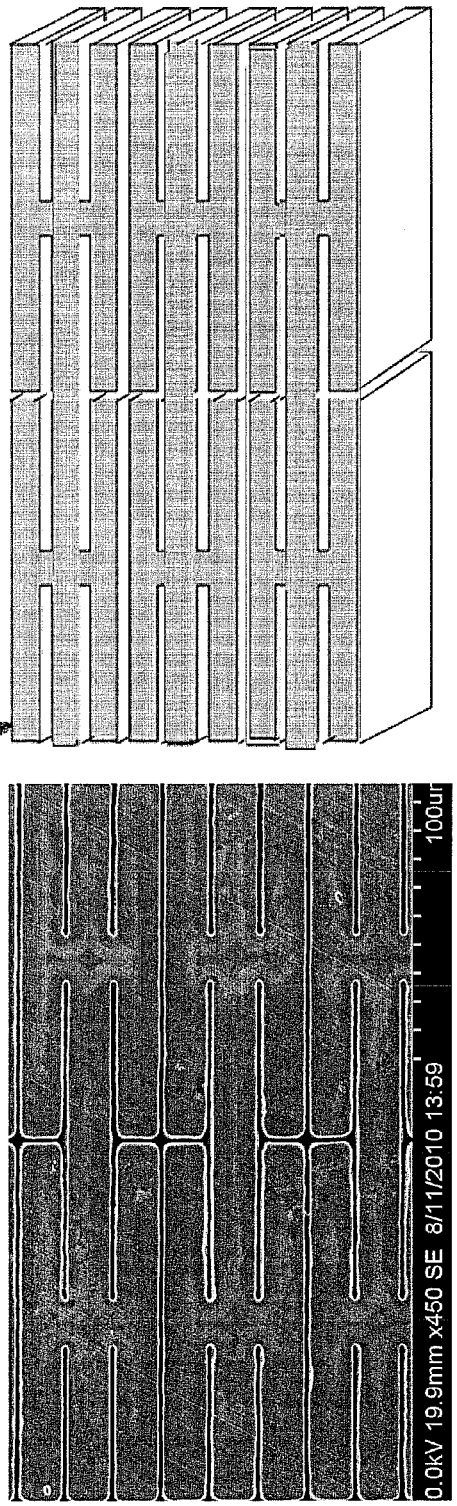
FIG. 7C

HIGH FREQUENCY PIEZOELECTRIC CRYSTAL COMPOSITES, DEVICES, AND METHODS FOR MANUFACTURING THE SAME

CROSS REFERENCE TO RELATED APPLICATIONS

This application relates to and claims priority from U.S. Provisional Ser. No. 61/344,801 filed Oct. 13, 2010 and International Ser. No. PCT/US2011/056230 filed Oct. 13, 2011, the entire contents of each of which are incorporated herein by reference.

FIGURE SELECTED FOR PUBLICATION

FIG. 3

BACKGROUND OF THE INVENTION

Field of the Invention

The present invention relates to the field of piezoelectric crystals and piezoelectric crystal composites operating for high frequency (>20 MHz). More particularly, the present invention provides high frequency piezoelectric crystal composites for high resolution imagery for preferred use in industrial and medical ultrasound applications, and even more particularly to the methods of manufacturing the same.

Description of the Related Art

Conventionally, PMN-PT based piezoelectric single crystals have superior dielectric and piezoelectric properties compared to the traditional PZT ceramics. To more fully exploit the excellent properties of single crystals, crystal composites have been fabricated to improve the electromechanical coupling coefficient and thus transducer performance characteristics.

For ultrasound transducers, the operating frequency is inversely related to the thickness of the piezoelectric material. Thus, as the targeted operating frequency increases, the thickness of piezoelectric material decreases accordingly this induces operative and electro mechanical difficulties. On the other hand, an optimal aspect ratio has been attempted for the piezoelectric crystal pillars in order to maintain the high electromechanical coupling coefficient of piezoelectric composite. To accommodate the requirements in thickness and aspect ratio, the feature size of the piezoelectric material in the high frequency composite needs to be reduced to meet the optimal ratio.

One attempt has been provided for such medical applications of micromachined imaging transducers known generally from U.S. Pat. No. 7,622,853 (Rehrig et al., assigned to SciMed Life Systems, Inc.), the entire contents of which are incorporated herein by reference.

As noted in U.S. Pat. No. 7,622,853, a medial device is provided with a transducer assembly including a piezoelectric composite plate formed using photolithography micromachining. The particular steps in the '853 patent are noted therein. The '853 patent additionally notes the conventional challenges of micromachining poled PZT ceramics, but fails to adjust to the now appreciated challenges noted below and additionally includes the detrimental impacts of electric field and clamping effect on strain. There is now appreciated a need for further imagery resolution and sensitivity over a depth that cannot be achieved.

Finally, it is further recognized that a high frequency transducer is typically driven at a higher electrical field compared to a low frequency transducer.

Accordingly, there is a need for an improved high frequency piezoelectric crystal composite, optionally related devices, and further optionally methods for manufacturing the same.

Related publications include the following, the entire contents of each of which are incorporated herein fully by reference:
1. P. Han, W. Yan, J. Tian, X, Huang, H. Pan, "Cut directions for the optimization of piezoelectric coefficients of PMN-PT ferroelectric crystals", Applied Physics Letters, volume 86, Number 5 (2005).
2. S. Wang, et al., "Deep Reactive Ion Etching of Lead Zirconate Titanate Using Sulfur hexafluoride Gas", J. Am. Ceram. Soc., 82(5) 1339-1341, 1999.
3. A. M. Efremov, et al., "Etching Mechanism of Pb(Zr, Ti)$O_3$ Thin Films in $Cl_2$/Ar Plasma", Plasma Chemistry and Plasma Processing 2(1), pp. 13-29, March 2004.
4. S. Subasinghe, A. Goyal, S. Tadigadapa, "High aspect ratio plasma etching of bulk Lead Zirconate Titanate", in Proc. SPIE—Int. Soc. Opt. Engr, edited by Mary-Ann Maher, Harold D. Stewart, and Jung-Chih Chiao (San Jose, Calif., 2006), pp. 61090D1-9.

ASPECTS AND SUMMARY OF THE INVENTION

In response, it is now recognized for the present invention that improved PMN-PT based piezoelectric crystal composites and for methods for manufacturing composite crystal elements required and are provided herein.

The present invention generally relates to high frequency piezoelectric crystal composites, devices, and method for manufacturing the same. In adaptive embodiments an improved imaging device, particularly a medical imaging device or a distance imaging device, for high frequency (>20 MHz) applications involving an imaging transducer assembly is coupled to a signal imagery processor. Additionally, the proposed invention presents a system for photolithography based micro-machined piezoelectric crystal composites and their uses resulting in improved performance parameters.

The present invention additionally relates to imagery devices, particularly medical devices and especially to improved medical imaging devices and systems that employ the proposed novel structures of crystal composite and composite crystal elements.

It is a further aspect of the present invention that the innovative fabrication approaches make the commercial production of crystal composite feasible and practical. The high frequency crystal composite (20 MHz to >100 MHz, and a thickness electro-mechanical coupling factor $k_t$ 0.65-0.90 can be used for medical ultrasound imaging and diagnosis with significantly improved performances. The high frequency crystal composite is especially applicable to use with skin, eye, intravascular, intracardiac, intracranial, intracavity or intra-luminal medical diagnosis devices. Such devices may be used in applications involving dermatology, ophthalmology, laparoscopy, intracardiac and intravascular ultrasound.

There is a further aspect of the invention that recognizes the use of crystal with a high coercive field (EC) when transducer excitation field is also high. In one alternative aspect of the present invention, ternary crystals Pb(In½Nb½)O3-Pb(Mg⅓Nb⅔)O3-PbTiO3 (PIN-PMN- PT) and other PMN-PT based crystals are recognized as having improved thermal and electrical properties than the binary PMN-PT crystal. As a consequence, an alternative embodiment of the invention employs a crystal composite based on these crystals which it is now recognized inherit the improved properties of the ternary crystals.

In one aspect of the particular invention there is provided a piezoelectric PMN-PT based crystal composites, having the crystal composition represented by the formula I: x*Pb(B'½B"½)O3-y*PbTiO3-(1-x-y)*Pb(Mg⅓Nb⅔)O3, where, x is defined as molar % 0.00 to 0.50; and y is defined as molar % 0.00 to 0.50, B' represents Indium (In), Ytterbium (Yb), Scandium (Sc) or Iron (Fe), B" represents Niobium (Nb) or Tantalum (Ta). Additionally, formula I be combined with additives Manganese (Mn) of up to 5% (wt %) and/or Cerium (Ce) of up to 10% (wt %) of a total batch weight.

In one aspect of the particular invention there is provided a piezoelectric PMN-PT based crystal composites, having the crystal composition represented by the formula II: x*ABO3-y*PbTiO3-(1-x-y)*Pb(Mg⅓Nb⅔)O3, where, x is defined as molar % 0.00 to 0.50; and y is defined as molar % 0.00 to 0.50, A represents Lead (Pb) or Bismuth (Bi), B represents Indium (In), Ytterbium (Yb), Iron (Fe), Zirconium (Zr), Scandium (Sc), Niobium (Nb), Tantalum (Ta), or a combination of the above elements. Additionally, formula II may be combined with additives Manganese (Mn) of up to 5% (wt %) and/or Cerium (Ce) of up to 10% (wt %) of a total batch weight.

In a further aspect of the invention piezoelectric crystal composites having formula I or II above are prepared by a method involving photolithograph based micromachining.

In a further aspect of the invention of the proposed invention as noted herein the composite posts proposed have an aspect ration of a post height (H) to an effective post width (W), H:W, of greater than 0.50, preferably greater than 1.0, and more preferably greater than 2.0

In a further aspect of the invention the proposed composite is a discontinuous hexagonal arrangement in a hybrid 1-3 configuration, and the piezoelectric crystal is (001) cut and poled in <001> direction.

In a further aspect of the invention, the proposed composite is a discontinuous hexagonal arrangement in a hybrid 1-3 configuration, and the piezoelectric crystal is (011) cut and poled in <011> direction, wherein polymeric fill lines extend in +/−32.5° (+/−2.5°) away from <10$\bar{1}$> direction.

In a further aspect of the invention, the proposed composite is parallelogram hybrid 2-2/1-3 configuration, and the piezoelectric crystal is (011) cut and poled in <011> direction, wherein polymeric fill lines extend in +/−32.5° (+/−2.5°) away from <10$\bar{1}$> direction.

The above and other aspects, features, systems, methods, and advantages of the present invention will become apparent to one with skill in the art upon study of the following description read in conjunction with the accompanying drawings, in which like reference numerals designate the same elements. It is intended that all such additional systems, methods, features, compositions, and details included within this description, be within the scope of the invention, and be protected by the accompanying claims.

BRIEF DESCRIPTION OF THE DRAWINGS

FIG. 3 indicates that the micro strain is fully zero in the directions +/−32.5° (see arrows) between curves. Calculated using formula $d'_{31}=d_{31}*Cos(\theta)*Cos(\theta)+d_{32}*Sin(\theta)*Sin(\theta)$.

FIG. 7A is a schematic pattern drawing of the proposed hybrid 2-2/1-3 crystal composite of an (011) cut with the kerf filling line in the direction of +/−32.5° (+/−2.5°) relative to the <10$\bar{1}$> direction.

FIG. 7B is a top-view SEM image of an (011) cut hybrid 2-2/1-3 crystal composite as in FIG. 7A, in accordance with a preferred embodiment of the present invention.

FIG. 7C is a perspective view of FIG. 7A showing a schematic pattern drawing of the proposed hybrid 2-2/1-3 crystal composite of an (011) cut with the kerf filling line in the direction of +/−32.5° (+/−2.5°) relative to the <10$\bar{1}$> direction.

DETAILED DESCRIPTION OF THE PREFERRED EMBODIMENTS

Figure 1:
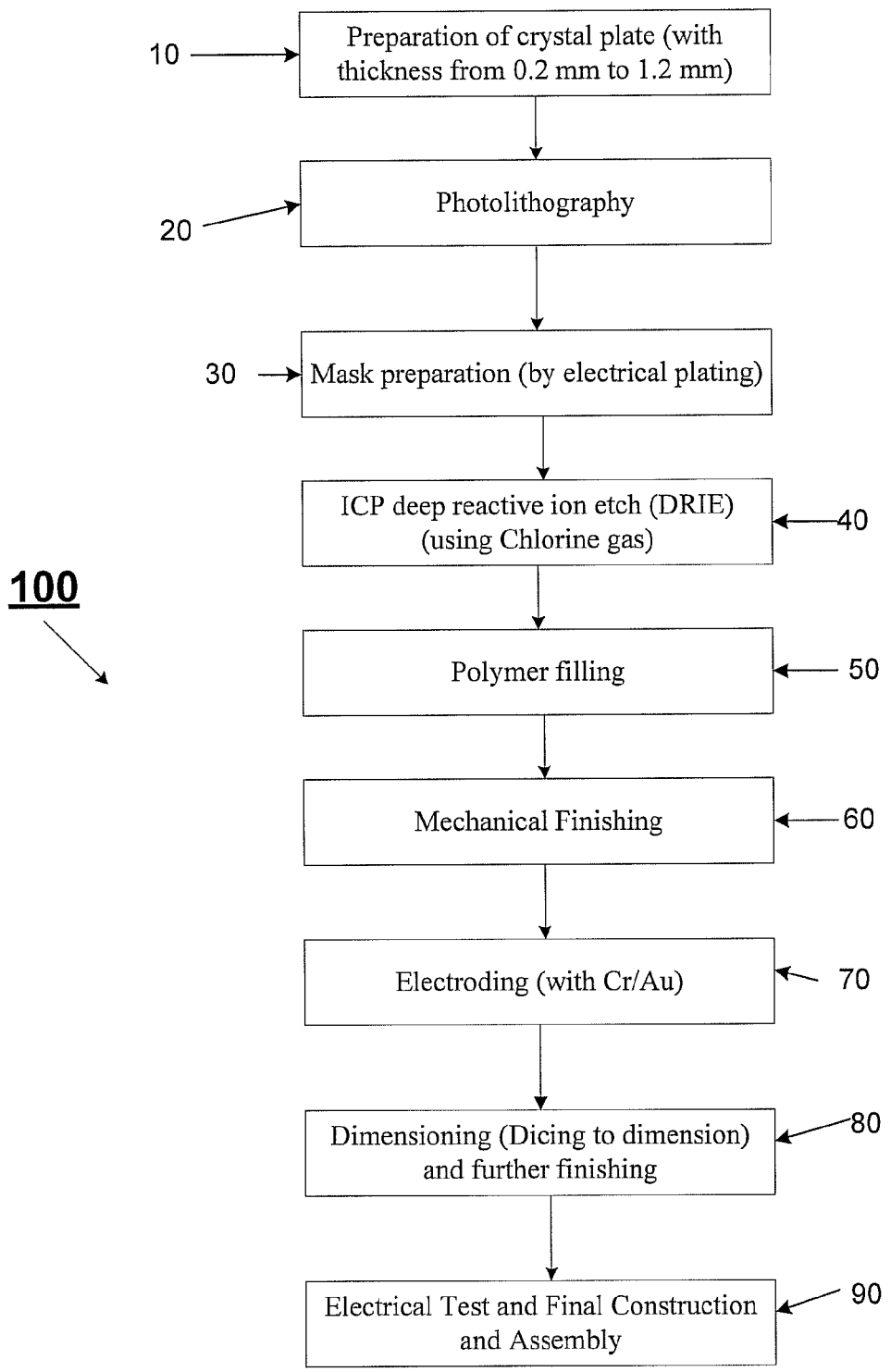
FIG. 1 is a process flow for a photolithography based micro machining process according to the present invention.

Reference will now be made in detail to embodiments of the invention. Wherever possible, same or similar reference numerals are used in the drawings and the description to refer to the same or like parts or steps. The drawings are in simplified form and are not to precise scale. For purposes of convenience and clarity only, directional (up/down, etc.) or motional (forward/back, etc.) terms may be used with respect to the drawings. These and similar directional terms should not be construed to limit the scope of the invention in any manner.

As will be used herein the Miller Indices identifiers serve as vector representations for orientation of an atomic plane in a crystal lattice having three axes represented by a set of 3 integer numbers, for example such conventional identifiers as, for example <010> or <10$\bar{1}$>, are used.

As will be further used herein, for example regarding the images of the present invention wherein polymeric (epoxy) regions are filled with a piezoelectrically non-active material, that the use of the phrase "kerf" is not limited to a region formed by a mechanical saw of any kind—instead the phrase "kerf" will be understood broadly by ones skilled in the art to represent the region between piezoelectric posts which receiving polymeric material, whether or not the actual region is formed by a saw, or by any other manufacturing process discussed herein.

Additionally, a description methodology (the M-N labeling convention) is used to describe the number of directions which each section of the piezoelectric material and polymeric material continuously extend, wherein M represents the number of continuous directions in which the piezoelectric (PMN-PT) material extends and N represents the number of directions in which the polymeric (epoxy) material continuously extends. While those of skill understand this convention, however as modified herein, the structures suggested herein have never been subjected to the M-N convention and therefore applicant requires a hybrid understanding wherein the directional extensions generally remain, but are discontinuous or interrupted, for example, by intersection with a cross directional polymeric material extending in a different and also discontinuous direction. In this manner, it will be understood that the (as later described) hexagonal structure involves discontinuous, interrupted, or hybrid polymeric (epoxy) material directions where the polymeric material direction is linear in only one direction along the length of the piezoelectric material itself and the other polymeric (epoxy) directions are interrupted-in-direction or discontinuous-in-direction by encountering piezoelectric material. One embodiment of the invention further has a structure the result of the piezoelectric material elements having discontinuous or interrupted side alignments with respective sides/edges of proximate piezoelectric material elements, so that sides/edges may not be coplanar (on the same plane) but may extend on parallel planes. Still a further embodiment of the invention does not contain simple regular unit elements (FIGS. 7A-7C for example), and instead requires a still further hybridization of the M-N convention.

This invention relates to the 20 MHz to >100 MHz high frequency piezoelectric single crystal composites/composite crystal elements and the process for the preparation thereof. The novel high-coupling factor crystal composites can broadly replace the legacy materials such as piezoelectric ceramics, single crystal and traditional crystal composite for high frequency transducers.

Referring now to FIG. 1 a process flow for a photolithography based micro machining process 100 is discussed. In the first step 10, a plate or block of piezoelectric single-crystal material (shown later), such as PMN-PT (Lead Magnesium Niobate-Lead Titanate) based crystals, such as binary solid solution PMN-PT and ternary solid solution PIN-PMN-PT (Lead Indium Niobate-Lead Magnesium Niobate-Lead Titanate) or PYbN-PMN-PT (Lead Ytterbium Niobate-Lead Magnesium Niobate-Lead Titanate) or these crystals above with dopants (Mn, Ce, Zr, Fe, Yb, In, Sc, Nb, Ta, and others). Such ternary crystals of the PMN-PT based piezoelectric crystals are now recognized as having improved thermal stability and increased coercive field that allows a higher driving electrical field.

The crystal composite and the composite crystal elements have novel structures and/or new crystallographic cut directions. The crystal composites can be fabricated by proprietary procedures including photolithography, deep reactive ion etching, fine mechanical finishing and electrode coating.

The plate (not shown) is preferably lapped on both sides and polished on one of the sides. The lapped and unpolished side can then be bonded to a glass carrier (not shown), which is bonded to a silicon, Si, wafer (not shown). The dimensions of the plate are in the range of ten (10) millimeters ("mm")× ten (10) mm×0.20 mm-to-1.20 mm in thickness; however, the dimensions could be of any size.

The material of the plate is a single crystal with electroded faces oriented along the <001> or <011> crystallographic directions. As one of ordinary skill in the art would appreciate, a single crystal structure can desirably have a high piezoelectric coefficient (e.g., $d_{33}$>2000 pC/N, $d_{33}$>0.8, $d_{33}'$>0.7). The plate preferably has a dielectric constant in the range of approximately 4000 to >7700 and a dielectric loss of less than 0.01.

It will be recognized that the plate piezoelectric single crystal is a ternary crystal formed according to the following formulas I or II:

Formula I: x*Pb(B'½B"½)O3-y*PbTiO3-(1-x-y)*Pb(Mg⅓Nb⅔)O3, where, x is defined as molar % 0.00 to 0.50; and y is defined as molar % 0.00 to 0.50, B' represents Indium (In), Ytterbium (Yb), Scandium (Sc) or Iron (Fe), B" represents Niobium (Nb) or Tantalum (Ta). Additionally, formula I may be combined with additives Manganese (Mn) of up to 5% (wt %) and/or Cerium (Ce) of up to 10% (wt %) of a total batch weight.

Formula II: x*ABO3-y*PbTiO3-(1-x-y)*Pb(Mg⅓Nb⅔)O3, where, x is defined as molar % 0.00 to 0.50; and y is defined as molar % 0.00 to 0.50, A represents Lead (Pb) or Bismuth (Bi), B represents Indium (In), Ytterbium (Yb), Iron (Fe), Zirconium (Zr), Scandium (Sc), Niobium (Nb), Tantalum (Ta), or a combination of the above elements. Additionally, formula II may be combined with additives Manganese (Mn) of up to 5% (wt %) and/or Cerium (Ce) of up to 10% (wt %) of a total batch weight.

Several non-limited examples of formulae I and II are found in the following table. It will be recognized that any composition matching the formulae I or II is included herein by reference as a suitable composition.

| | Formula I | Formula II |
|---|---|---|
| Example 1 | 31% PIN-46.7% PMN-20.8% PT | 15% BiScO-58.6% PMN-26.4% PT |
| Example 2 | 15% PIN-53.7% PMN-22.4% PT:8.9% Ce | 15% BiScO-57.6% PMN-26.4% PT:1% Ce |
| Example 3 | 25% PYbN-45.7% PMN-25% PT:2% Mn | 10% BiScO-58.6% PMN-26.4% PT:5% Mn |
| Example 4 | 10% PZrT-64% PMN-24% PT:3% Mn | 7% BaTiOs-61% PMN-PT-32% PT |

In a second step 20 of photolithography a thin metal (Nickel) seed layer was applied and then in a step 30 a mask was prepared by spincoating a photoresist on top of the seed layer. The mask defines the desired shape and/or pattern of imaging element(s) within the piezoelectric composite material. After baking, UV exposure, and development, a patterned photoresist was obtained.

A Nickel mask of a predetermined thickness (here 10 microns, but can be any thickness from 1 to 30 microns) was electroplated thereon to have the inverse pattern of the mask of the photoresist, which was then stripped away using reactive ion etching. The use of hard or high molecular weight metals such as Ni and Pt, is desirable for selectivity to protect the covered underlying area of the plate from being later etched.

The etching process, such as reactive ion etching ("RIE") is used as noted, but other etching processes can be used, such as wet-etching. In one preferred embodiment, chlorine, $Cl_2$ based RIE etching is used, which has an etching rate of approximately from less than 3 microns/hour to 12 microns/hour and can cause a substantially vertical etching profile (e.g., >89 degree). In the alternative, or in addition, to $Cl_2$, sulfur hexafluoride, $SF_6$, based etching can be used, which has similar etching properties to that of $Cl_2$. The nickel, Ni, pattern protects the underlying portions of the plate covered by the pattern from the etching process.

In a step 40 the crystal parts with the patterned etched mask were located into an ICP-plasma unit for deep reactive ion etching (DIRE) using the preferred $Cl_2$ gas. As a result of step 40, one or more deep posts of the type discussed later are formed in the plate with one or more kerfs bounding each respective post, etched in the uncovered portions of the plate. The one or more kerfs can have a width in the range of approximately from less than one (<1) to twelve (12) microns, and preferably from 1 to 10 microns in width.

The respective posts can have a width ranging from approximately 3 to 200 (or longer in length for the hybrid 2-2/1-3 configuration discussed herein) microns and have a height in the range of approximately less than five (<5) to more than seventy (>70) microns, such that in one embodiment, it is preferable to have an aspect ratio (post height/post width) of at least one to dampen the effect of lateral modes. For the dimensions of the plate described above, the etching process can last approximately six (6) to eight or eighteen (8 or 8) hours. After the etching step 40, the plate is then rinsed with a solvent for cleaning.

In the next step 50, the kerfs are filled with an epoxy, such as Epoxy 301 provided by Epo-Tek, although other epoxies may be employed without departing from the scope and spirit of the present invention. A vacuum (not shown) may be utilized to remove air bubbles and prevent any void within the kerfs. In the next step 60, after the epoxy cures, the top portion of the plate and epoxy are lapped to a thickness of approximately 25 microns. In a step 70, an electrode pattern is then applied to the plate to form the imaging transducer pattern. The electrode pattern is preferably comprised of gold (Au) and/or chromium (Cr). Moreover, as one of ordinary skill in the art would appreciate, electronic circuitry, such as imaging processing circuitry, (not shown) can be bonded to the electrodes (not shown). Further, the electrode pattern formed on the plate can define any pattern of imaging transducers, including an array, e.g., an imaging transducer at each post, or a single imaging transducer. An epoxy layer may be applied to the back of the plate.

In a further step 80 the plate is dimensioned suitably as desired and then poled at 50 VDC. In a step 90 key dielectric and piezoelectric properties are measured and calculated with suitable equipment, for example Agilent 4294A Precision Impedance Analyzer.

Imaging transducers having an operating frequency at above 20 MHz, e.g., to >100 MHz, can be developed using photolithography based micromachining, such as the process 100 described above. The higher frequency of operation increases the resolution and image depth of an imaging transducer. Furthermore, the bandwidth of the imaging transducer, particularly when single crystal PMN-PT is employed as the piezoelectric, can be close to 100%, compared to only 70 to 80% for <20 MHz transducers made with PZT ceramic.

The greater bandwidth improves the transducer's axial resolution, which increases the imaging depth. This is desirable for high frequency transducers, which have very limited imaging depth due the strong attenuation of high frequency ultrasound in tissue. When single crystal is used, these advantages can be achieved with sensitivities equivalent to or better than ceramic transducers. These high frequency transducers can be applied to a number of medical procedures including the imaging of the anterior region of an eye for monitoring surgical procedures such as cataract treatment by lens replacement and laser in situ keratomileusis (LASIK) and tumor detection (preferably up to sixty (60) MHz for fifty (50) .mu.m resolution); skin imaging for care of burn victims and melanoma detection (preferably twenty five (25) MHz for subcutaneous, fifty (50) MHz for dermis and one hundred plus (100+) MHz for epidermis); intra-articular imaging for detection of pre-arthritis conditions (preferably twenty five (25) to fifty (50) MHz); in-vivo mouse embryo imaging for medical research (preferably fifty (50) to sixty (60) MHz); Doppler ultrasound for determination of blood flow in vessels<one hundred (100) .mu.m in diameter (preferably twenty (20) to sixty (60) MHz); intracardiac and intravascular imaging (preferably ten (10) to fifty (50) MHz); and ultrasound guidance for the biopsy of tissue.

Figure 2:
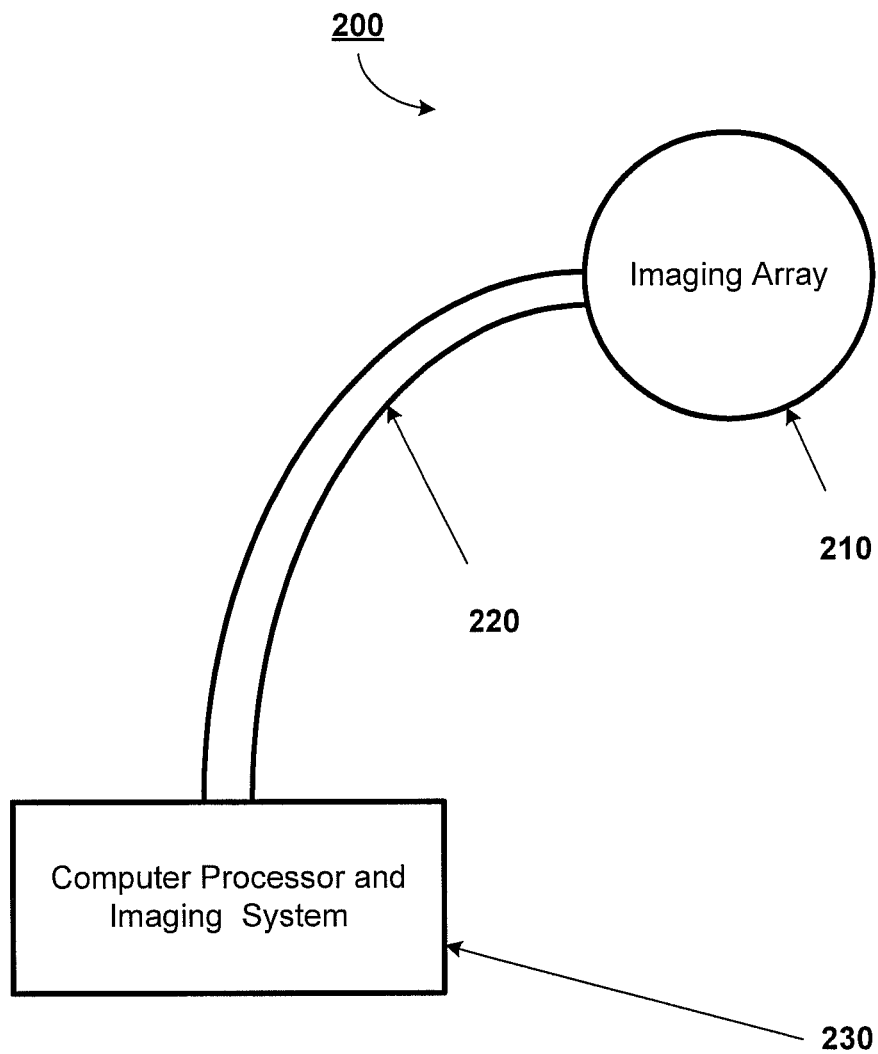
FIG. 2 is an illustrative schematic view of an imaging transducer arrangement operatively coupled with a digital transducer signal processor for operatively imaging the signals from the imaging transducer.

As an example of such a medical device, we refer not to FIG. 2, wherein an exemplary medical treatment transducer device 200 includes an array (not shown) of transducers is joined with an exemplary array (not shown) of the proposed inventive piezoelectric posts (not shown) in a form (shown circularly) suitable for use in a catheter or guidewire of some type. An exemplary guidewire and signal conduit 220 transmit received imagery signals to a computerized processing and imaging system 230 for display of the received imaging signals. The conduit 220 may be formed in any conventional form operative for the purpose. For example it may be formed of polymer or metal construction and contain multiple signal or control wires to operatively join a treatment end with the imagery display comptroller.

The present inventors have determined that the PMN-PT based piezoelectric crystals usually use (001)-cut and poling <001> which gives the highest $d_{33}$ but the lateral clamping effect by the epoxy filled into kerfs cannot be avoided and his highly detrimental to performance for a variety of imaging systems and methods of use. We first use the hexagonal ("bee nest") type hybrid shaped 1-3 type crystal composite. The advantage is significant in that the structure is mechanically much stronger and more stable than square-shaped pattern if the both piezo-effective volume is the same. It is much more practical/suitable for large scale fabrication.

Figure 3:
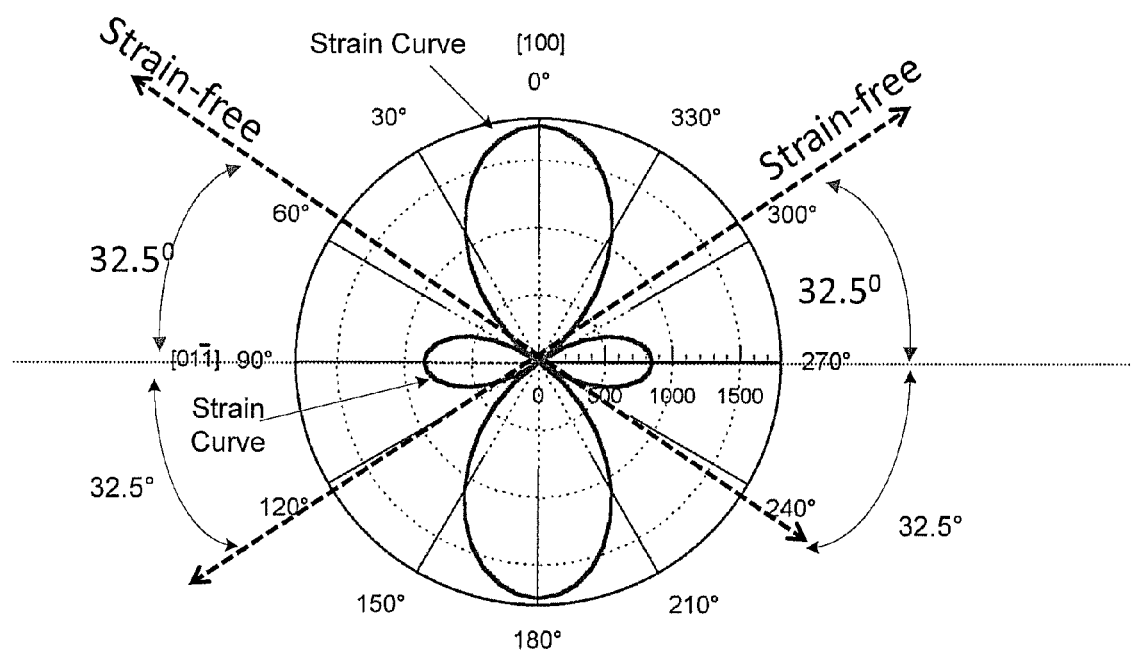
FIG. 3 is a 2-dimensional plot for calculated value of $d_{31}$ on (011) plane (the plane out of the paper) for a PMN-PT crystal.

Referring now to FIG. 3, it was determined as particularly suitable the (011)-cut and poled PMN-PT based crystal for particularly high frequency transducers. The advantage is the lateral clamping effect by the epoxy in kerfs can be totally avoided if the kerf filling in the direction of +/−32.50° (+/−2.5°) is used in a direction away from the <10$\bar{1}$> direction.

We have induced the formula (I) to calculate the $d_{31}$ by coordination rotation:

$$d'_{31}=d_{31}*\mathrm{Cos}(\theta)*\mathrm{Cos}(\theta)+d_{32}*\mathrm{Sin}(\theta)*\mathrm{Sin}(\theta) \quad (1)$$

From the 2-D plot of the $d_{31}$, it is indicated that the micro strains are zero in the +/−32.50° directions away from the <10$\bar{1}$> direction. It is a significant advantage that the lateral strain-free arrangement will greatly enhance the electromechanical coupling factor and broaden the bandwidth permissible in an ultrasound device.

Figure 4A:
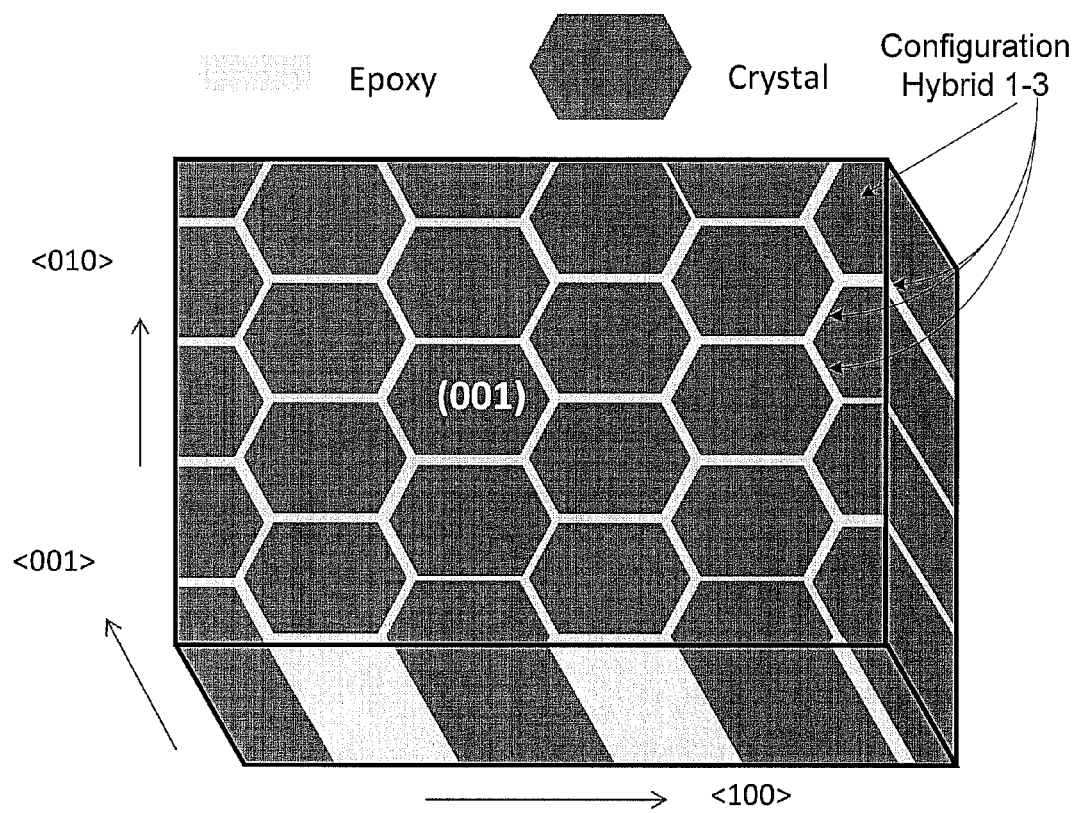
FIG. 4A is an illustrative perspective schematic of a hybrid 1-3 crystal composite for a transducer having a hexagonal structure, <001> cut, noting directional orientation and epoxy polymer and crystal designations with no impact on clamping direction due to <001> cut.
Figure 4B:
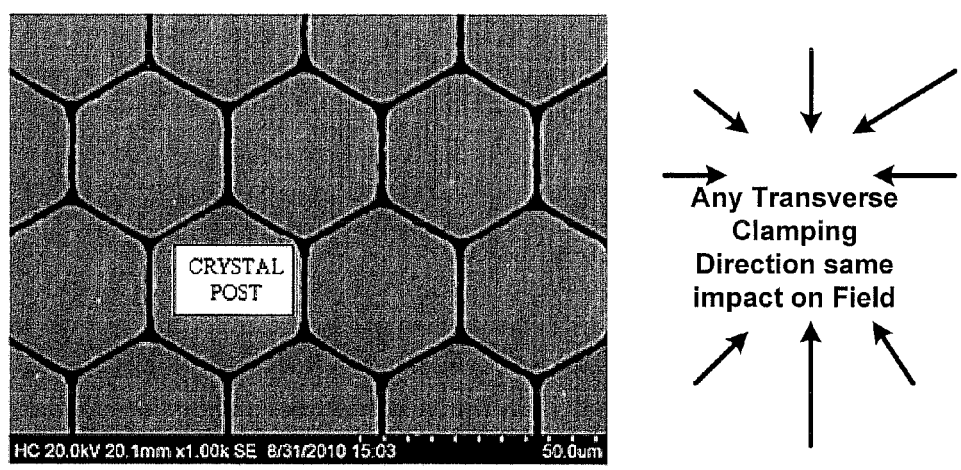
FIG. 4B it a top-view SEM image of a 1-3 crystal composite of FIG. 4A for a transducer having a hexagonal structure, <001> cut, thickness 30 μm, wherein the black lines are understood as kerfs filled with an epoxy polymer, in accordance with a preferred embodiment of the present invention.

Discussion of FIGS. 4A to 4B a schematic and SEM image of a hexagonal hybrid 1-3 crystal composite structure having an (001) cut. Here the 'hybrid' phrase is used for M-N configuration as for the first time discontinuous kerf lines are used and for the first time hexagonal crystal posts are used. As a result, this aspect of the invention is isotropic, and the field/clamping effect is substantially the same in any direction since the kerf is parallel to the poling direction. Perspective view FIG. 4A illustrates directional orientation and hybrid M-N arrangement for discontinuous or interrupted polymeric material arrangements. The SEM image of FIG. 4B is shown having a thickness of 30 microns. As noted, in view of the (001) cut and a poling at <001> direction, the clamping effect is substantially uniform in any direction (see illustrative arrows) and the reliability of the piezoelectric crystal composite is greatly enhanced since failure direction must be non-linear and the clamping effect is also not directionally dependent.

Figure 5A:
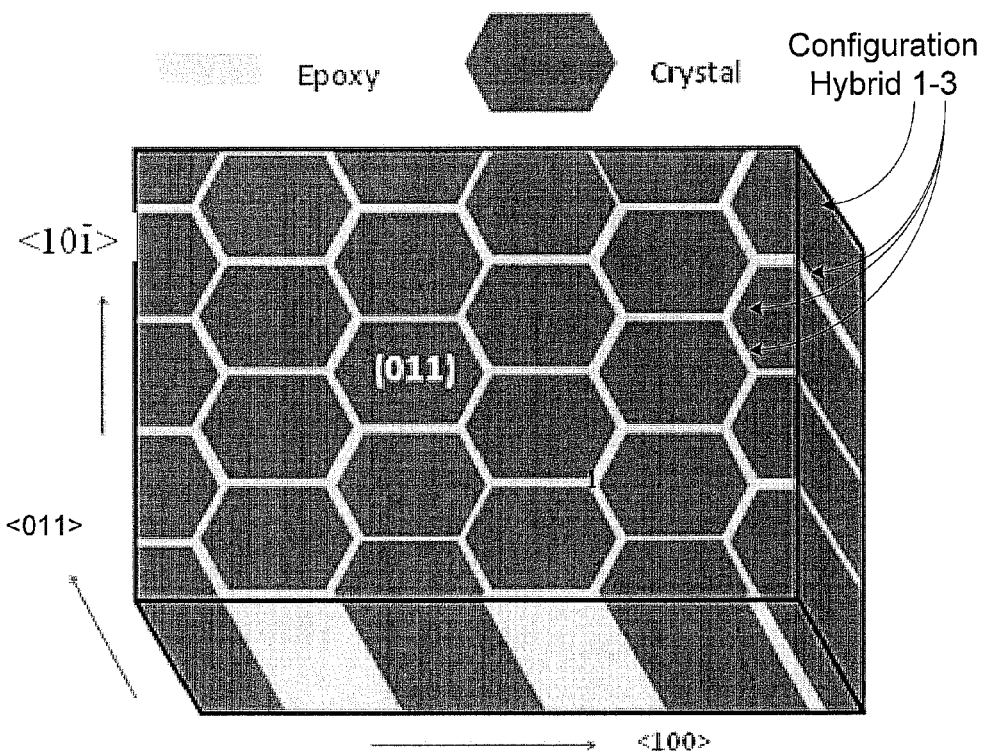
FIG. 5A is an illustrative perspective schematic of a 1-3 crystal composite for a transducer having a hexagonal structure, <011> cut, noting directional orientation and epoxy polymer and crystal designations
Figure 5B:
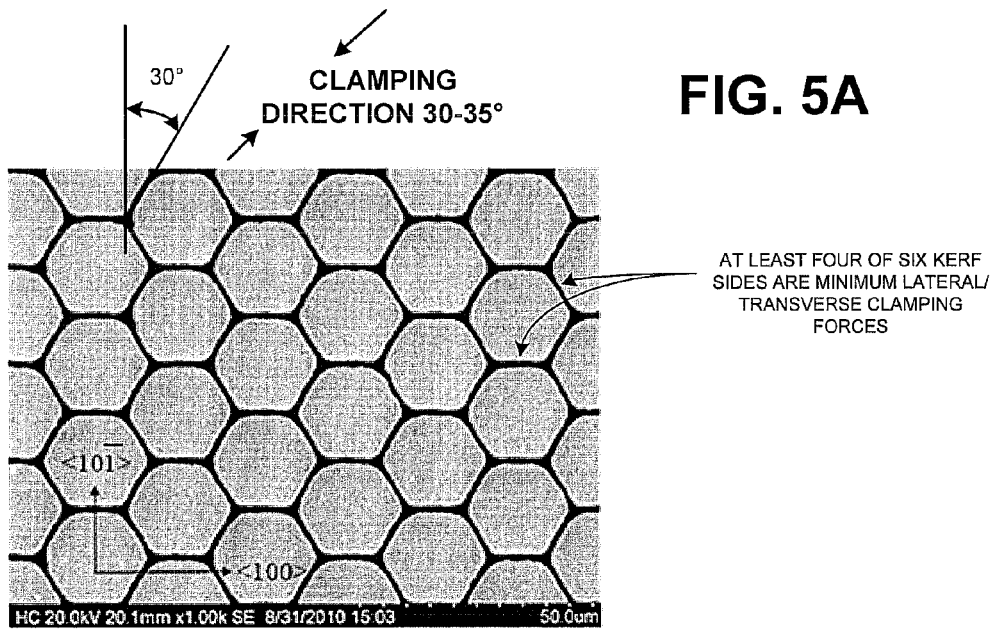
FIG. 5B is a top-view SEM image of a hybrid 1-3 crystal composite of FIG. 5A for a transducer having a hexagonal structure, <011> cut, thickness 22 μm, wherein the black lines are kerfs filled with an epoxy polymer, in accordance with a preferred embodiment of the present invention.

Referring now to FIGS. 5A and 5B a schematic and SEM image of a hexagonal hybrid 1-3 crystal composite structure having a completely new (011) cut. Perspective view FIG. 5A illustrates directional orientation and hybrid M-N arrangement for discontinuous or interrupted polymeric material arrangements. Here the 'hybrid' phrase is used for M-N configuration as for the first time discontinuous kerf lines are used and for the first time hexagonal crystal posts are used, particularly new with the (011) cut direction. The SEM image of FIG. 5B is shown having a thickness of 22 microns. As noted, in view of the (011) cut and a poling at <011> direction, the clamping direction is desirably 30-35° from <10$\bar{1}$> direction, and preferably about 32.5° (+/−2.5°) from the <10$\bar{1}$> direction. In this alternative embodiment, at least one kerf is guaranteed to be free of any clamping effect while the reliability of the piezoelectric crystal composite is greatly enhanced since failure direction must be non-linear.

Figure 5C:
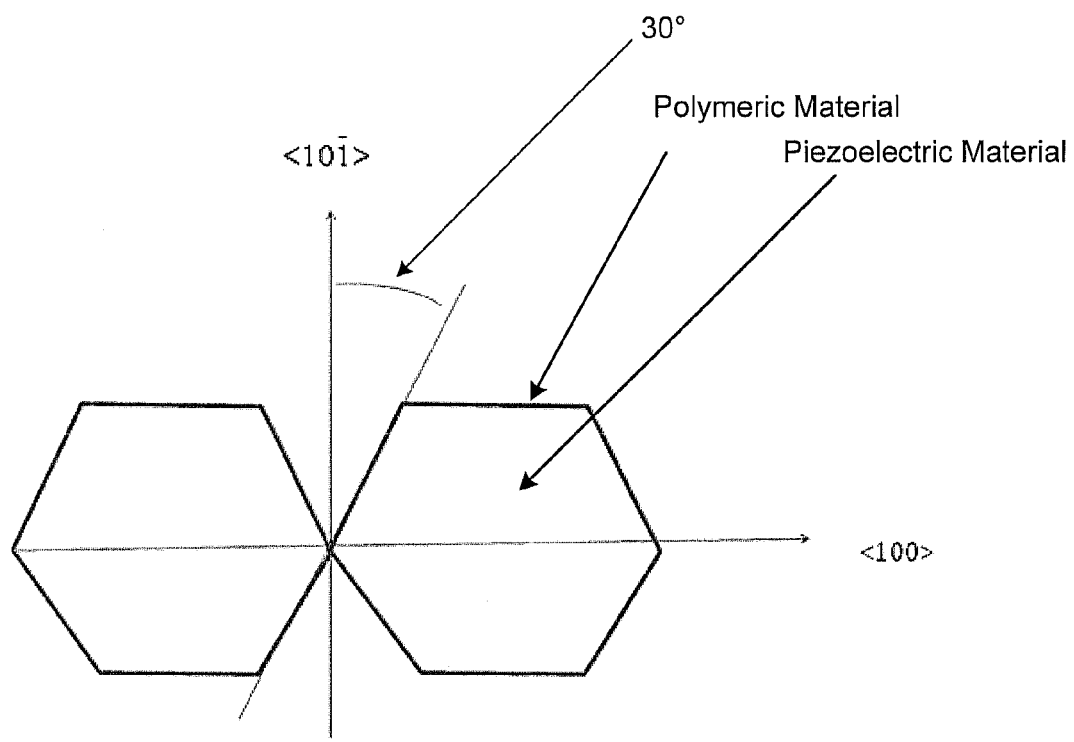
FIG. 5C is an illustrative orientation drawing noting the kerf orientation at the identified 30°, and a clamping direction between 30° and 35°, and preferably +/−32.5° from the <10$\bar{1}$> direction orientation for a hexagonal polygon arrangement as in FIGS. 5A and 5B.

Referring now to FIG. 5C a schematic illustrative orientation drawing noting the kerf orientation at the identified 30° from the <10$\bar{1}$> direction for the hexagonal hybrid 1-3 configuration, and a clamping direction between 30° and 35°, and preferably +/−32.5° from the <10$\bar{1}$> direction, as noted in FIGS. 5A and 5B. It will also be recognized that the same 30° understanding off a designated direction is suitable for FIGS. 4A and 4B albeit from a different (001) cut direction.

Figure 5D:
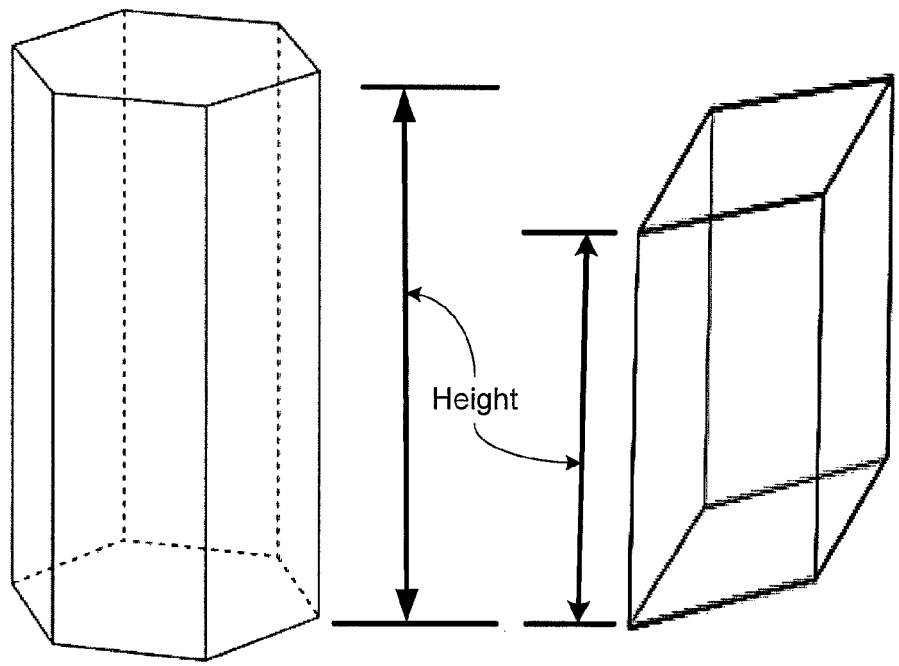
FIG. 5D is an illustrative dimensioning guide regarding calculating effective post widths where not square, here, an average width is calculated from the diagonal widths and heights for aspect ratio considerations.
Figure 5D:
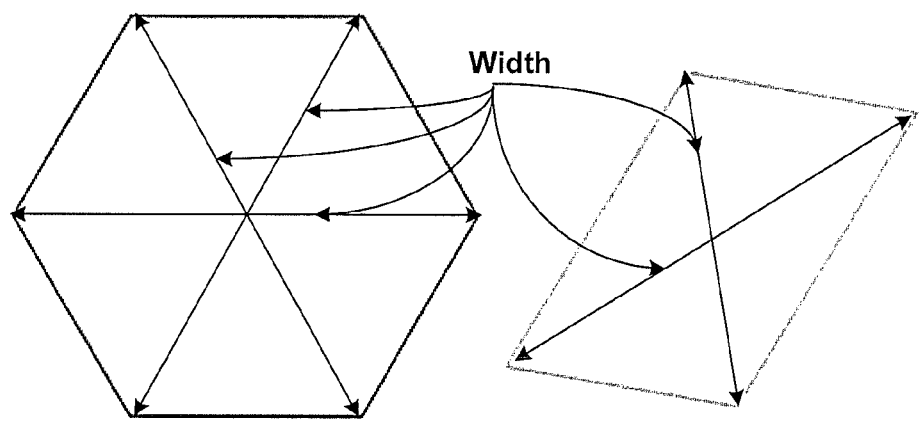

Referring now to FIG. 5D, is an illustrative dimensioning guide regarding calculating effective post widths where not square, as here in a hybrid 1-3 configuration. As noted, either a hexagonal or parallelogram configuration designates a single height of the piezoelectric crystal material and can be measured. Regarding each cross sectional view, there are multiple diagonals (either generally uniform as in the hexagon or non-uniform as in the parallelogram). On either configuration, multiple width measurements are taken and an average is calculated for determination of an aspect ratio (Height:Width) of preferably greater than 0.50, more preferably greater than 1.0, and more preferably greater than 1.5 or 2.0. However, each ideal ratio is dependent upon the other configurations, composition details, and device or method requirements. For example, one preferred alternative embodiment includes a specific ratio of less than 2. As a further detail, it will be noted (for example with the hybrid 2-2/1-3 configuration of FIGS. 7A to 7C, that such aspect ratios are no longer applicable. It will also be understood that typically a desired kerf width is between 1 micron to 10 microns.

As a result of preparing such composites according to the details herein throughout, a thickness electromechanical coupling factor $k_t$ of 0.65-0.90 is achieved.

Figure 6A:
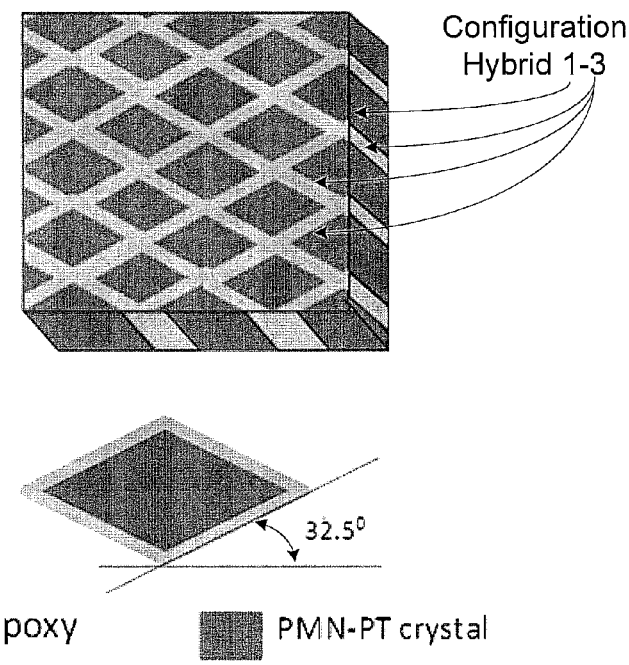
FIG. 6A is an illustrative perspective schematic of a 1-3 crystal composite for a transducer having a parallelogram (diamond) structure, to minimize the transverse clamping effect by the epoxy polymer filled kerfs, in accordance with a preferred embodiment of the present invention.
Figure 6B:
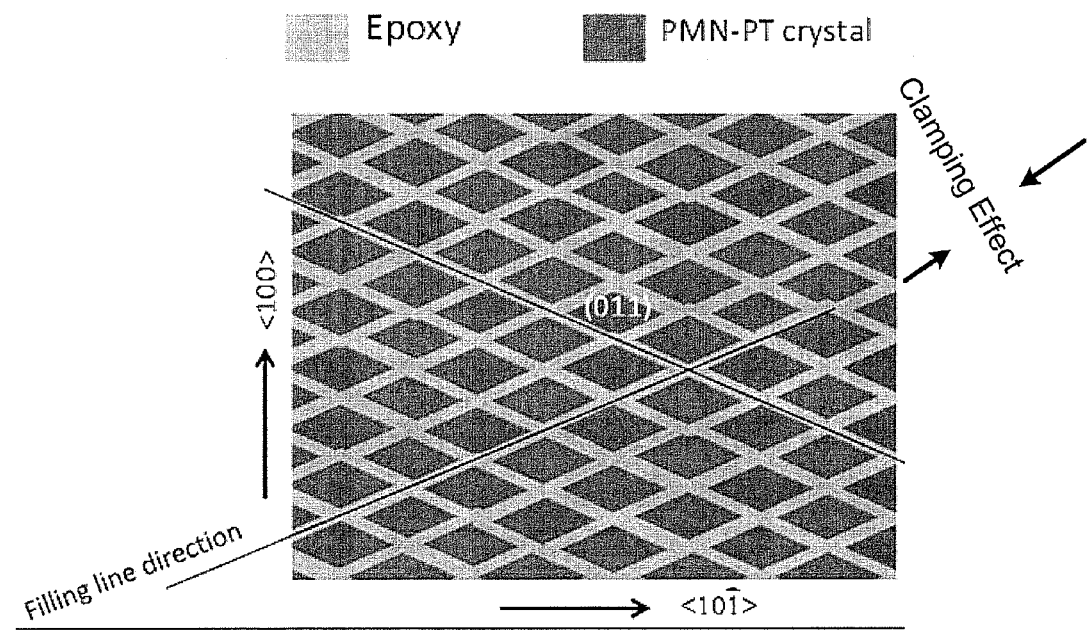
FIG. 6B is an illustrative plan view in (011) cut of a hybrid 1-3 crystal composite (of FIG. 6A) for a higher coupling factor wherein the transverse epoxy polymer filled kerfs are made at +/−32.5° (+/−2.5°) are therefore strain free. The clamping effect direction is noted.

Referring now to FIGS. 6A and 6B an alternative parallelogram hybrid 1-3 configuration is presented with an (011) cut and a <011> poling direction where the kerf lines run at 30-35° away from the <10$\bar{1}$> cut, and preferably at 32.5°+/−2.5°. This configuration minimizes the transverse clamping effect by the epoxy filled into the kerfs between the parallelogram shaped crystal posts. Based upon this hybrid 1-3 configuration the composite crystal provides a high coupling factor, wherein the epoxy kerfs are transverse strain free. Here the 'hybrid' phrase is used for M-N configuration as for the first time continuous kerf lines are used in a parallelogram pattern with the kerf lines being 115° apart relative to a respective plane. This arrangement fully cancels the lateral clamping effect.

Referring now to FIGS. 7A to 7C. Here a schematic, SEM, and perspective view of a further discontinuous hybrid 2-2/1-3 configuration is provided with repeated units shown, wherein the crystal is (011) cut and <011> poled. As graphically illustrated, the kerf filling line direction is preferably 30-50° and more preferably 32.5° (+/−2.5°) away from the <10$\bar{1}$> direction. As a result of this discontinuous hybrid 2-2/1-3 configuration the clamping direction (shown) has no negative impact on performance. It is noted that the white spaces in FIGS. 7A, 7C and the black spaces in FIG. 7B represent epoxy or polymeric material, and the bars represent piezoelectric material. It is noted that the transverse extension strain is negative parallel to the <011> direction and positive parallel to the <011> direction.

As noted herein with regards to FIGS. 7A to 7C, each individual unit member (shown) is a unique geometry for smooth packing while simultaneously allowing for allowing gas outwardly during epoxy infusion. Each unit member includes a central elongate web bar (shown) extending in a first direction from a first end to a second end. Respective bridge members or bridge portions (shown) extend perpendicularly from the elongate web bar on opposing sides (shown) and intermediate the respective first and second ends, forming a total of four bridge member parts, two on each side of the web bar (shown). Extending from each of the four bridge member parts are leg bars (shown), each leg bar parallel to the web bar and spaced therefrom by a kerf width. In this configuration, it is thus understood that the hybrid 2-2 configuration portion represents the parallel web bars and leg bars, each spaced by polymeric material, and the hybrid 1-3 configuration portion represents the interaction of the crossing bridge members and bridge member parts and the polymeric material cross-passages at the end of each leg bar. As a result, those skilled in the art will recognize the hybrid 2-2/1-3 configuration as fully understood in conjunction with the drawings.

It will be understood that the method of fabricating noted earlier may be used to fabricate one of more imaging transducers having any of the hybrid configurations with any composition shown herein without departing from the scope of the entire disclosure. It will be understood that the compositions may be used in any configuration.

It will be understood that an imaging device may be configured as discussed in FIG. 2, and may be formed in any hybrid configuration in any composition shown herein without departing from the scope of the entire disclosure. It will be understood that the compositions may be used in any configuration.

It will be understood that the phrase hexagonal is a polygon with six edges or sides in a plan view, such that the hexagonal polygons of the type shown have six edges or sides and extend from an initial position.

It will be understood that there are many different kinds of quadrilateral (four sided) polygons, and all have several things in common: two opposing sides are coplanar, have two diagonals, and the sum of their four interior angles equals 360 degrees, however as noted herein, the phrase parallelogram used herein reflects two parallel pairs of opposite sides without right angles, and a rhombus is merely such a parallelogram with equal length sides (and may also be referred to as a 'diamond' pattern or an oblique rhombus) with understanding by those of skill in the art.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents. As a further example, each feature of one embodiment can be mixed and matched with other features shown in other embodiments, and similarly features may be added or removed such that the invention is recognized as not restricted except in view of the appended claims.

What is claimed:

1. A piezoelectric PMN-PT based crystal composite, said piezoelectric crystal composite having a crystal composition with one lead-free component, and being represented by the formula:

$x*ABO_3-y*PbTiO_3-(1-x-y)*Pb(Mg_{1/3}Nb_{2/3})O_3;$ wherein,
x is defined as molar % 0.00 to 0.50;
y is defined as molar % 0.00 to 0.50;
A represents Bismuth (Bi) or Barium (Ba);
B represents one selected from the group consisting of: Indium (In), Ytterbium (Yb), Iron (Fe), Zirconium (Zr), Scandium (Sc), Niobium (Nb), Tantalum (Ta), and a combination of these elements,
wherein when said crystal composite is (011) cut and <011> poled and provides zero strain in the direction of +/−32.5° (+/−2.5°) away from the <011> direction according to the coordinate rotation $d_{31}$ formula:

$d'_{31}=d_{31}*Cos(\theta)*Cos(\theta)+d_{32}*Sin(\theta)*Sin(\theta).$

2. The piezoelectric al composite, according to claim 1, in further combination with:
an additive, said additive being selected from the group consisting of: Manganese (Mn) of up to 5% (wt %) and Cerium (Ce) of up to 10% (wt %) of a total batch weight.

3. The piezoelectric crystal composite, according to claim 2, wherein:
said crystal composite has a thickness electromechanical coupling factor $k_t$ of about 0.65 to 0.90.

4. The piezoelectric crystal composite, according to claim 1, wherein:
said crystal composite is operative at a frequency of at least 20 MHz.

5. The piezoelectric crystal composite, according to claim 4, wherein:
said crystal composite is operative at a frequency of at least 80 MHz.

6. The piezoelectric crystal composite, according to claim 1, in further combination with:
a medical imaging device configured for operative ultrasound imaging.

* * * * *